United States Patent [19]
Kokubu

[11] Patent Number: 6,162,052
[45] Date of Patent: Dec. 19, 2000

[54] MEDICAL LASER HANDPIECE

[75] Inventor: Shinji Kokubu, Sendai, Japan

[73] Assignee: J. Morita Manufacturing Corporation, Kyoto, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/015,435

[22] Filed: Jan. 29, 1998

[30] Foreign Application Priority Data

Jan. 31, 1997 [JP] Japan ................................. 9-031442

[51] Int. Cl.[7] ............................. A61B 17/36; A61N 5/06
[52] U.S. Cl. ............................ 433/29; 433/224; 606/16
[58] Field of Search ........................... 433/29, 81, 215, 433/224, 229; 606/15, 16

[56] References Cited

U.S. PATENT DOCUMENTS

| | | | |
|---|---|---|---|
| 4,243,388 | 1/1981 | Arai | 433/224 |
| 4,666,405 | 5/1987 | Ericson | 433/229 |
| 5,017,134 | 5/1991 | Saito et al. | 433/224 |
| 5,207,576 | 5/1993 | Vassiliadis et al. | 433/215 |
| 5,236,360 | 8/1993 | Levy | 433/215 |
| 5,310,344 | 5/1994 | Vassiliadis et al. | 433/215 |
| 5,324,200 | 6/1994 | Vassiliadis et al. | 433/224 |
| 5,342,198 | 8/1994 | Vassiliadis et al. | 433/215 |
| 5,503,559 | 4/1996 | Vari | 433/224 |
| 5,797,740 | 8/1998 | Lundvik | 433/29 |

FOREIGN PATENT DOCUMENTS

| | | |
|---|---|---|
| S61-40419 | 9/1986 | Japan . |
| H4-54460 | 8/1992 | Japan . |

*Primary Examiner*—Ralph A. Lewis
*Attorney, Agent, or Firm*—Koda & Androlia

[57] ABSTRACT

A laser handpiece is configured by a main body 13 and a laser probe 10 mounted on the tip end of the main body 13. The laser probe 10 has an emission fiber 12. A laser beam generated by a laser beam source is emitted from an emission end portion 22 of the emission fiber 12. The emission end portion 22 of the emission fiber 12 is formed into a circular conical shape. The laser beam emitted from the emission end portion 22 contains a first laser beam which is emitted in the axial direction of the emission fiber 22, and a second laser beam which is emitted in a ring-like shape in a radial direction of the emission fiber 12.

11 Claims, 11 Drawing Sheets with the laser beam. Therefore, the dentin of the root canal
MEDICAL LASER HANDPIECE

BACKGROUND OF THE INVENTION

1. Field of the Invention

The present invention relates to a laser handpiece which is held by an operator to use for the performance of treatments such as a dental treatment.

2. Description of the Related Art

In the field of dental treatment, for example, a in which root canal preparation in which part of a tooth to be ground. In the root canal preparation, a rotating reamer is inserted into a root canal and a dentin of the root canal wall is ground. The root canal preparation is conducted with, for example, an object for removing any infection which has entered a dental tubule. In the root canal preparation, the dentin of the root canal wall must be removed by a thickness which is constant in a peripheral direction. Usually, a root canal has a section of a nearly long elliptic shape. Therefore, when the dentin is circularly ground by using a reamer, a normal portion of the dentin which is not required to be ground is also ground. In the treatment using a reamer, processes are used such as: (1) anesthetization; (2) opening of the pulp chamber; (3) extirpation of pulp; (4) root canal debridement by using several kinds of reamers; (5) processing of root canal tip end by using a fine reamer; (6) disinfection; (7) drying; and (8) gutta-percha filling. Such process produce problems such as the treatment is difficult to conduct, and the treatment requires a prolonged time period. In such a treatment using a reamer, recently, the treatment itself is greatly advanced by a combination of the treatment and the measurement of a root canal length. However, the fundamental technique, i.e., grinding by using a reamer is not advanced at all. Among dental treatments, particularly, a root canal preparation treatment has unstable factors because it is impossible for an operator perform the treatment while visually inspecting the site to be treated. As a result, the root canal preparation is considered as one of the most difficult treatments.

Under such circumstances, recently, a laser treatment using a laser beam has been developed in the field of dental treatment. In a treatment using a laser beam, a laser handpiece is used which comprises a main body and a laser probe attached to the main body. A laser beam generated by a laser beam source is emitted from an emission end portion of the laser probe. In a treatment using a laser beam, evaporation and sterilization processes by the laser beam irradiation can be conducted on the dentin and soft tissues (including a gingivae, a dental pulp, etc.).

In addition to the dental treatment field, treatments using a laser beam are known in other fields, too. An example of such treatments is a treatment of pollinosis in which the cortex of the nasal cavity is irradiated with a laser beam, such as a $CO_2$ laser beam, so as to conduct evaporation or coagulation. In such a treatment of pollinosis, if the laser beam irradiation is conducted in a wrong direction, normal tissues are destroyed. Therefore, such a treatment involves a heavy risk depending on the irradiation direction.

An example of a laser probe which is used in such a laser treatment is proposed in Japanese Examined Patent Publication JP-B2 4-54460 (1992). For example, the laser probe is used in an operation of anastomosing blood vessels which were accidentally cut, in a short time period. In such an operation, cut sections of blood vessels are butted against each other, and the butted portions are irradiated with an annular laser beam from the inside of a blood vessel. In order to emit such a laser beam, the emission end portion of the laser probe has a circular conical shape. The laser beam which has been totally reflected by one oblique wall face of the emission end portion is emitted through the other oblique wall face which is at the symmetrical position, thereby allowing the laser beam to be emitted in a ring zonal shape. According to this configuration, the butted portions of the blood vessels can be anastomosed by one irradiation.

Additionally there is known a laser knife which is disclosed, for example, in Japanese Examined Patent Publication JP-B2 61-40419 (1986). In the laser knife, an emission end portion through which a laser beam is emitted is formed into a circular conical shape, and a flat face of a small diameter is formed at the tip end of the emission end portion. Because of the above-mentioned configuration of the emission end portion, a laser beam of the laser knife is concentrically emitted from the tip end face of the emission end portion in the axial direction, and the linearly emitted laser beam is used for evaporation of vital tissues.

The laser probe disclosed in JP-B2 4-54460 has been developed with the object of anastomosis of cut blood vessels. In the laser probe, therefore, a laser beam is emitted only laterally from the emission end portion in a ring-like shape, and the laser beam is not substantially emitted in the forward and axial direction. If a laser beam is emitted from the emission end portion in the forward and axial direction, normal portions other than the butted portions of blood vessels are irradiated with the laser beam, so that the normal portions are adversely affected by the laser beam irradiation. therefore, the laser probe is not intended to emit a laser beam forward from the emission end portion.

In the laser knife disclosed in JP-B2 61-40419, a fiber probe is not used. Therefore, the laser knife cannot be used in a treatment in which a laser knife is to be inserted into a narrow space, such as a dental treatment. In addition, because of the configuration for the use as a laser knife, the laser beam is emitted forward from the emission end portion in the axial direction. Therefore, the laser knife is not intended to emit a laser beam in a ring-like shape in a lateral direction with respect to the emission end portion.

In a dental treatment, for example, a root canal treatment, the dentin of a site facing a narrow space must be evaporated. In the case of root canal preparation, for example, when a laser probe is inserted into a root canal, the emission end portion of the laser probe is directly opposed to the root apex. When a laser beam is emitted laterally from the emission end portion of laser probe in a ring-like shape as disclosed in, for example, JP-B2 4-54460, the dentin of the root canal wall at the root apex, and the dental pulp in the apical dental foramen at the root apex cannot be irradiated wall at the root apex, and the dental pulp in the apical dental foramen cannot be evaporated. When a laser beam is emitted forward from the emission end portion of the laser probe in the axial direction as disclosed in JP-B2 61-40419, the dentin of the root canal wall at the root apex and the dental pulp in the apical dental foramen can be evaporated, but the evaporation cannot be conducted on the whole periphery of the root canal. Under these circumstances, in the field of a dental treatment, it has been eagerly requested to develop a laser handpiece having a fiber probe which enables the dentin of the root canal wall in the range from the root canal orifice to the apical dental foramen to be evaporated as required.

SUMMARY OF THE INVENTION

It is an object of the invention to provide a medical laser handpiece capable of evaporating a narrow site as required, and of being preferably applied to dental treatments.

In a first aspect of the invention, a medical laser handpiece comprises a main body and a laser probe attached to the main body, the laser probe including an emission fiber, a laser beam generated by a laser beam source being emitted from an emission end portion of the emission fiber, wherein the emission end portion of the emission fiber is formed into a circular conical shape, and from the emission end portion are emitted a first laser beam in an axial direction of the emission fiber and a second laser beam in a ring-like shape in a radial direction of the emission fiber.

According to the first aspect of the invention, from the emission end portion of the emission fiber are emitted a first Laser beam in an axial direction of the emission fiber, and a second laser beam in a ring-like shape in a radial direction of the emission fiber. In a dental treatment, for example, when the main body of the hand piece is held and the emission end portion of the emission fiber is inserted into a root canal, it is possible to evaporate the dentin of sites which are in front of and at the side of the emission end portion. In the root canal preparation treatment, for example, even the dentin of the root canal wall at the root apex, and the dental pulp in the apical dental foramen can be evaporated by the first laser beam emitted from in the axial direction of the emission fiber. Since the second laser beam is emitted in a ring-like shape in the radial direction of the emission fiber, the dentin of the root canal wall and the dental pulp over the whole periphery of the root canal in the range from the root canal orifice to the root apex can be evaporated only by inserting the probe into the root canal. As a result, since the dental pulp can be evaporated by the second laser beam in the same manner as the root canal debridement, the laser handpiece can be applied also to the extirpation of the pulp. Moreover, dental canaliculi are formed in a root canal and elongate in a direction which is nearly perpendicular to the root canal. When the second laser beam is emitted in a ring-like shape in the radial direction of the emission fiber, also the interior of such a dental canaliculus can be irradiated with the second laser beam so as to be sterilized.

In a second aspect of the invention, an apex angle of the emission end portion of the emission fiber is in a range of 60 to 93 degrees.

According to the second aspect of the invention, since the apex angle of the emission end portion of the emission fiber is in the range of 60 to 93 degrees, from the emission end portion of the emission fiber are emitted a first laser beam in the axial direction and a second laser beam in a ring-like shape in the radial direction of the emission fiber. Accordingly the laser handpiece can be preferably used in the above-mentioned dental treatment.

In a third aspect of the invention, an apex angle of the emission end portion of the emission fiber is in a range of 60 to 90 degrees.

According to the third aspect of the invention, since the apex angle of the emission end portion of the emission fiber is in the range of 60 to 90 degrees, the second laser beam emitted from the emission end portion is radially emitted in a range from a direction which is oriented diagonally forward with respect to the axial direction, to a direction which is nearly perpendicular to the axial direction. In the root canal preparation in a dental treatment, for example, the dentin of the root canal wall and the dental pulp over the whole periphery of the root canal can be evaporated as required, and also dental canaliculi can be irradiated with the beam.

In a fourth aspect of the invention, the apex angle of the emission end portion of the emission fiber is in a range of 70 to 80 degrees.

According to the fourth aspect of the invention, since the apex angle of the emission end portion of the emission fiber is in the range of 70 to 80 degrees, the first laser beam emitted from the emission end portion is emitted in the axial direction, and the second laser beam is emitted in a ring-like shape in the radial direction which is nearly perpendicular to the axial direction. Furthermore, the tip end of a reamer used in a reamer processing has an angle of about 70 degrees, which is nearly equal to the apex angle of the emission end portion. Therefore, even the tip end of the reamer processing can be irradiated with the laser beam.

In a fifth aspect of the invention, the second laser beam emitted from the emission end portion of the emission fiber is emitted in a radial direction nearly perpendicular to the axis of the emission fiber.

According to the fifth aspect of the invention, the second laser beam emitted from the emission end portion of the emission fiber is emitted in a radial direction nearly perpendicular to the axis of the emission fiber. Consequently, in the root canal preparation in a dental treatment, for example, the dentin of the root canal wall and the dental pulp over the whole periphery of the root canal can be evaporated as required.

In a sixth aspect of the invention, the first laser beam emitted from the emission end portion of the emission fiber is emitted in a ring-like shape in the axial direction of the emission fiber.

According to the sixth aspect of the invention, the first laser beam emitted from the emission end portion of the fiber probe is emitted in a ring-like shape in the axial direction of the emission fiber. Consequently, in the root canal preparation in a dental treatment, for example, the whole periphery of the tip end of a reamer can be irradiated with the laser beam.

In a seventh aspect of the invention, 1 to 20% of a laser beam entering the emission fiber is emitted as the first laser beam from the emission end portion, and 80 to 99% of the laser beam is emitted as the second laser beam from the emission end portion.

According to the seventh aspect of the invention, since 1 to 20% of a laser beam entering the emission fiber is emitted as the first laser beam and 80 to 99% of the laser- beam is emitted as the second laser beam, the energy densities of the first and second laser beams are not largely different from each other. In a dental treatment, for example, the dentin in front of and at the side of the emission end portion of the emission fiber can be evaporated in an approximately uniform manner.

In an eighth aspect of the invention, 5 to 15% of the laser beam entering the emission fiber is emitted as the first laser beam from the emission end portion, and 85 to 95% of the laser beam is emitted as the second laser beam from the emission end portion.

According to the eighth aspect of the invention, since 5 to 15% of a laser beam entering the emission fiber is emitted as the first laser beam and 85 to 95% of the laser beam is emitted as the second laser beam, the energy densities of the first and second laser beams are nearly equal to each other. In a dental treatment, for example, the dentin in front of and at the side of the emission end portion of the emission fiber can be evaporated in a nearly uniform manner.

In a ninth aspect of the invention, an electrode made of an electrically conductive material is disposed on an outer periphery of the emission fiber.

According to the ninth aspect of the invention, since an electrode is disposed on the outer periphery of the emission fiber, the electrode can be used as one contact terminal of a measuring instrument for measuring the electric resistance. When another contact terminal which is separately prepared is contacted with a predetermined site in a mouth and the emission fiber is inserted into a root canal, the resistance of a portion which extends between the electrode and the other contact terminal via the root apex can be measured. This resistance measurement enables the position of the emission end portion of the emission fiber in the root canal to be detected.

In a tenth aspect of the invention, the emission fiber has an outer diameter of 100 to 2,000 μm and the laser probe is a probe for a dental treatment.

According to the tenth aspect of the invention, the laser handpiece comprises an emission fiber of an outer diameter of 100 to 2,000 μm, and hence can be preferably used in a dental treatment.

BRIEF DESCRIPTION OF THE DRAWINGS

Other and further objects, features, and advantages of the invention will be more explicit from the following detailed description taken with reference to the drawings wherein.

DETAILED DESCRIPTION OF THE PREFERRED EMBODIMENTS

Figure 1:
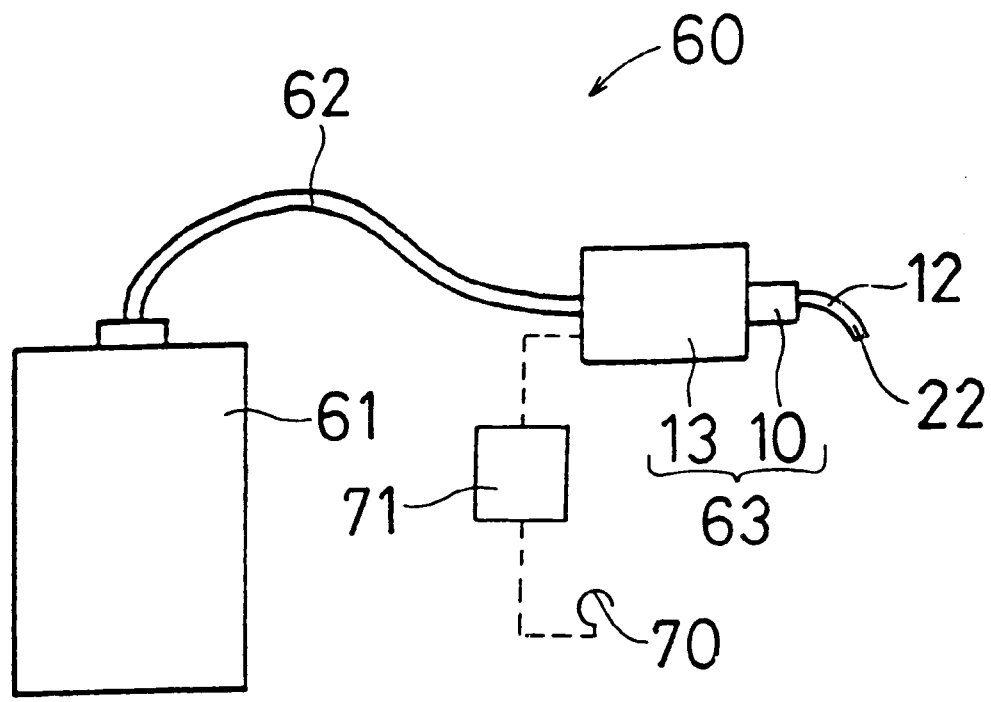
FIG. 1 is a block diagram schematically showing the configuration of a laser treatment apparatus provided with a laser handpiece of a preferred embodiment according to the invention.

Now referring to the drawings, preferred embodiments of the invention are described below.

FIG. 1 is a diagram schematically showing the configuration of a laser treatment apparatus provided with a medical laser handpiece of a preferred embodiment of the invention. Hereinafter, the laser handpiece of the embodiment applied to an apparatus for a dental treatment will be described. Referring to FIG. 1, the illustrated laser treatment apparatus 60 elementally consists of a laser beam source 61, a light-guiding path 62, and the laser handpiece 63. The laser beam source 61 generates a pulse laser beam having a wavelength of 2.0 to 4.0 μm, an output energy of 1 to 2,500 mJ, a pulse width of 1 nsec to 9 msec, and a pulse cycle of 1 to 200 pps. The laser beam is guided to the laser handpiece 63 via the light-guiding path 62.

The laser handpiece 63 comprises a main body 13 and a fiber probe 10 detachably mounted on the tip end of the main body 13. When the fiber probe 10 is mounted on the main body 13, the light-guiding path 62 is optically coupled with an emission fiber 12. The laser beam which is guided from the laser beam source 61 to the handpiece 63 via the light-guiding path 62 enters an incidence end of the emission fiber 12 of the probe 10, propagates to an emission end portion 22 through the emission fiber 12, and is then emitted from the emission end portion 22 in the manner described later.

The laser beam generated by the laser beam source 61 is easily absorbed by $H_2O$ and OH groups in vital tissues. When vital tissues are irradiated with the laser beam, the vital tissues of the irradiated site are instantaneously destroyed because of absorption and evaporation to $H_2O$ and OH groups. In such a treatment using the laser beam, a predetermined treatment can be performed under the state where a patient feels substantially no pain. Because of bacterioclasis due to the temperature at evaporation of $H_2O$ and OH groups, and absorption to $H_2O$ and OH groups contained in bacteria, a sterilization process can be conducted. Therefore, the amounts of chemicals for sterilization can be reduced to a very low level or substantially eliminated. Furthermore, the time period for sterilization can be shortened or substantially eliminated.

Figure 2:
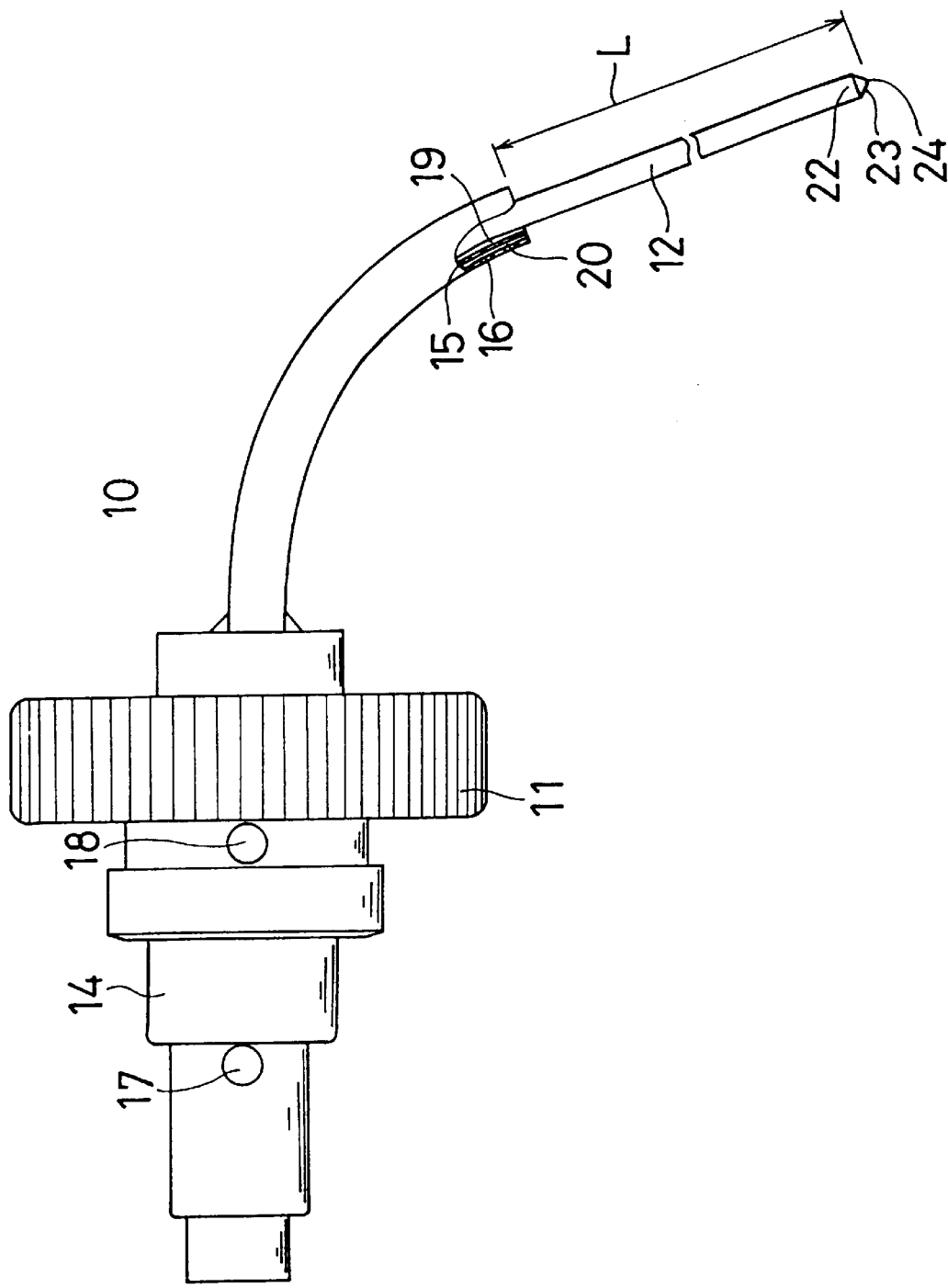
FIG. 2 is a partially cutaway front view showing a laser probe of the laser handpiece of FIG. 1.

Referring to FIG. 2, the laser probe 10 will be described. The illustrated laser probe 10 elementally consists of a probe body 11, and the emission fiber 12 which is held by the probe body 11. The probe 10 is detachably amounted on the main body 13, and used with being selected from several sorts of probes depending on the kind of the treatment to be performed.

The probe body 11 comprises an attaching unit 14 which is to be attached to the main body 13, and inner and outer tubes 15 and 16 which coaxially arcuately elongate from the attaching unit 14. The emission fiber 12 is passed through the inner tube 15 so as to be held thereby. Communicating flow paths 17 and 18 are formed at the attaching unit 14. A gap 19 is formed between the fiber 12 and the inner tube 15. The gap 19 is passed through the communicating flow path 17. A gap 20 is formed between the inner tube 15 and the outer tube 16. The gap 20 is passed through the communicating flow path 18. The gaps 19 and 20 open at the tip ends of the inner and outer tubes 15 and 16, respectively. The one communicating flow path 17 is connected to an air source (not shown) so that air from the air source is ejected toward the laser irradiation site through the communicating flow path 17 and the annular gap 19. The other communicating flow path 18 is connected to a water source (not shown) so that water from the water source is ejected toward the laser irradiation site through the communicating flow path 18 and the annular gap 20. In contrast, water may be supplied through the gap 19, and air may be supplied through the gap 20. In this way, water and air are mixed with each other to be ejected in a spray form to the laser irradiation site, or, depending on the kind of the treatment, air or water may be independently ejected, whereby the evaporation of the dentin can be accelerated. This ejection is conducted because of the following reasons. When water is ejected independently or with being mixed with air in a spray form, the absorption characteristics of a laser wavelength to $H_2O$ and OH groups can be enhanced, the heat generated in the absorption and evaporation to $H_2O$ and OH groups can be cooled, and dust produced by the destruction of tissues can be removed away.

The emission fiber 12 is held in such a manner that the incidence end which is not shown is positioned in the attaching unit 14, and linearly elongates from the inner tube 15 along the axis of the tip end of the inner tube 15 so that the emission end portion 22 is projected from the tip end of the inner tube 15. The projection distance L of the emission end portion 22 is set to be, for example, about 3 to 25 mm and preferably to be 10 mm or longer, and may be adequately selected in accordance with the kind of the treatment to be performed. The emission end portion 22 comprises a first portion which is formed into a circular conical shape pointed to the front, and a second portion which is disposed at the tip end of the first portion. The first portion defines a first emission face 23 of a circular conical shape, and the second portion defines a second emission face 24 which is formed at the circular conical tip end of the first emission face 23 so as to be continuous therewith. In the emission fiber 12, a laser beam enters the incidence end, and the incident laser beam is emitted from the first and second emission faces 23 and 24 of the emission end portion 22 as described later.

Figure 3:
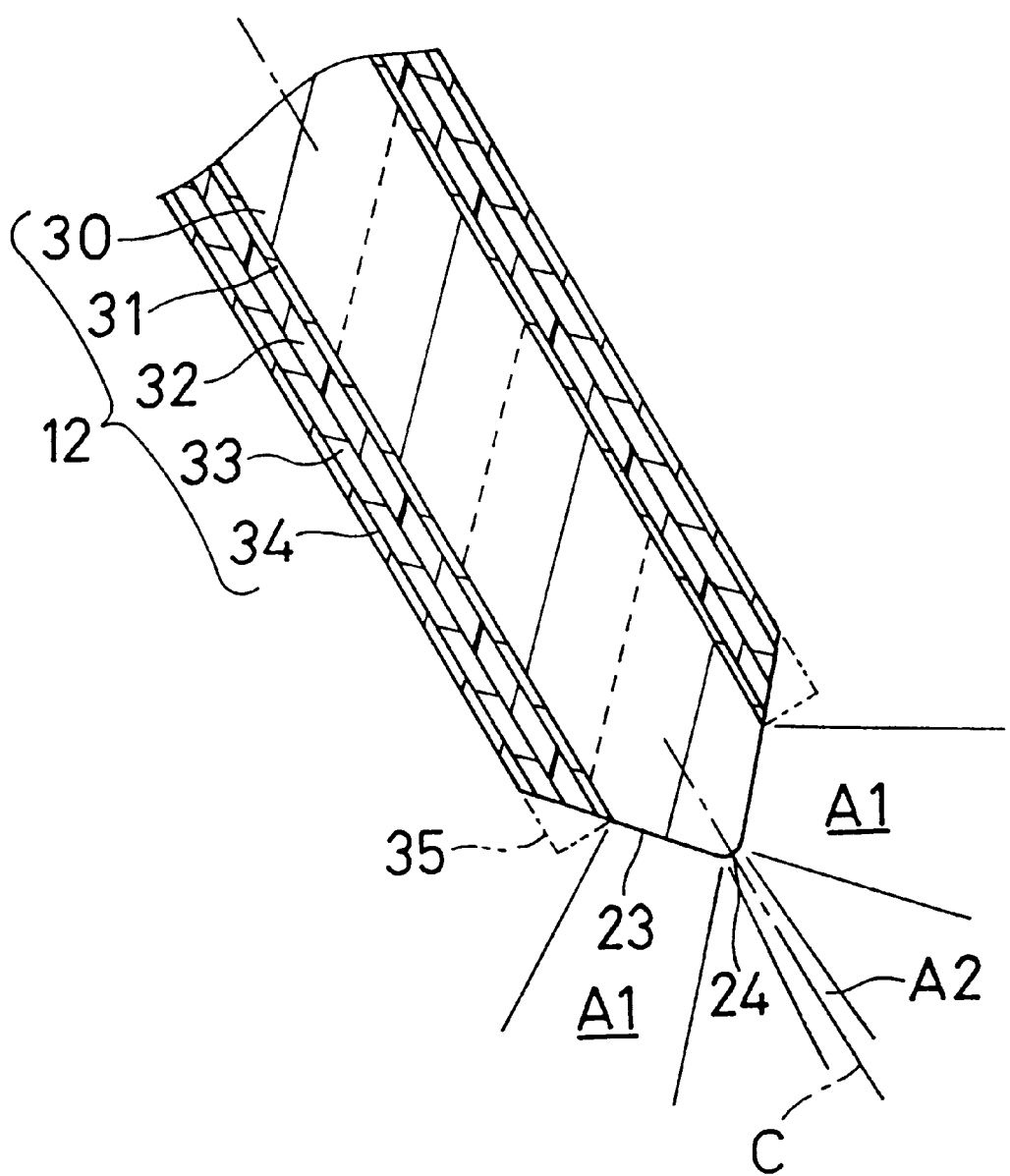
FIG. 3 is an enlarged sectional view of an emission end portion of an emission fiber of the laser probe of FIG. 2.

FIG. 3 is an enlarged section view of the emission end portion 22 of the emission fiber 12 and the vicinity of the emission end portion. Referring to FIG. 3, the emission fiber 12 has a center core 30, a clad 31 disposed on the outer periphery of the core 30, a first jacket 32 disposed on the outer periphery of the clad 31, a second jacket 33 disposed on the outer periphery of the first jacket 32, and an electrode 34 disposed on the outer periphery of the second jacket 33. The clad 31 is disposed so as to cover the whole of the outer peripheral face of the cylindrical core 30. The first jacket 32 is disposed so as to cover the whole of the outer peripheral face of the clad 31. The second jacket 33 is disposed so as to cover the whole of the outer peripheral face of the first jacket 32. The electrode 34 is disposed so as to cover the whole of the outer peripheral face of the second jacket 33. Alternatively, the electrode 34 may be formed on a part of the second jacket so as to form a linear or band-like form. In the case where the second jacket 33 is made of an electrically conductive material, the electrode 34 may be omitted. In this case, also the first jacket 32 may be omitted.

In order to allow the emission end portion 22 of the emission fiber 12 to be inserted into a narrow space, the outer diameter of the emission fiber 12 is selected to be in the range of 100 to 2,000 $\mu$m. In the embodiment, the outer diameter of the core 30 is set to be about 200 $\mu$m and that of the emission fiber 12 to be about 300 $\mu$m so that the probe can be preferably used in a dental treatment. The core 30 is made of, for example, quartz glass. The clad 31 is made of a material having a different refractive index from the core 30, such as a glass material. The first jacket 32 is made of a high polymer material such as a silicon resin, and the second jacket 33 is made of a metal material such as aluminum in order to prevent the emission fiber 12 from being broken. Alternatively, the second jacket 33 may be made of a high polymer material such as Teflon. The electrode 34 is formed by plating the outer peripheral face of the second jacket 33 with gold. In place of gold plating, a film or wire of another electrically conductive material may be formed. In the embodiment, the emission fiber 12 is formed into the five-layer structure. As described above, the emission fiber 12 may have any one of three- to five-layer structures. The emission fiber 12 of the five-layer structure includes the core 30, the clad 31, the first and second jackets 32 and 33, and the electrode 34. The tip end of the fiber is formed into a circular conical shape. Even when the fiber is inserted into a narrow space such as a root canal, for example, the fiber does not hitch, with the result that the fiber can be easily inserted into a dental pulp or the like. In the embodiment, in relation to the disposition of the electrode 34 to the emission fiber 12, the jacket is configured so as to have a two-layer structure. When the electrode 34 is not disposed, the emission fiber 12 may have a three-layer structure consisting of the core 30, the clad 31, and the first jacket 32. In the emission fiber 12 of this kind, the first jacket 32 is not always necessary and hence may be omitted.

In the emission fiber 12, a laser beam entering from the incidence end, such as Er-YAG (Erbium-Yttrium-Aluminum-Garnet) laser having a wavelength of 2.94 $\mu$m is guided to the emission end portion 22 with being reflected by the boundary between the core 30 and the clad 31, and then emitted from the first and second emission faces 23 and 24. The first and second emission faces 23 and 24 are formed at the tip end of the core 30. The laser beam propagates in the core 30 and is then emitted from the tip end thereof. From the above, in the tip end of the emission fiber 12, only the core 30 is required to be formed into a tapered shape, and the other components, i.e., the clad 31, the first and second jackets 32 and 33, and the electrode 34 may be formed so as to have an end face which is perpendicular to an optical axis C, or the axis of the core 30 (in other words, the emission fiber 12) as shown by phantom lines 35.

As described above, the first emission face 23 has a tip end of a tapered shape, i.e., a circular circular conical shape. Through the first emission face, a part of the laser beam is emitted outward and laterally so as to form a ring-like irradiation shape over the whole periphery with respect to the optical axis C which coincides with the axis of the core 30. In other words, a part of light entering the incidence end of the emission fiber 12 can be emitted to, for example, a region A1 shown in FIG. 3. As described above, the second emission face 24 is continuous with the first emission face 23 and forms at the tip end a predetermined shape, in the embodiment, a spherical shape. Through the second emission face, the remaining part of the laser beam is emitted forward in a circular shape along the optical axis C. In other words, the remaining part of the light entering the incidence end of the emission fiber 12 can be emitted to, for example, a region A2 shown in FIG. 3 in a plane including the optical axis C. The laser beam emitted to the region A2 mainly contains the light emitted from the second emission face 24, and partly contains also the light which is emitted forward from the first emission face 23. In this way, from the emission fiber 12, a laser beam entering the incidence end of the emission fiber is emitted as a first laser beam in the direction of the optical axis C, i.e., the axial direction of the emission fiber 12, and also as a second laser beam in a ring-like shape and outward, laterally, and radially with respect to the emission fiber 12.

Figure 4:
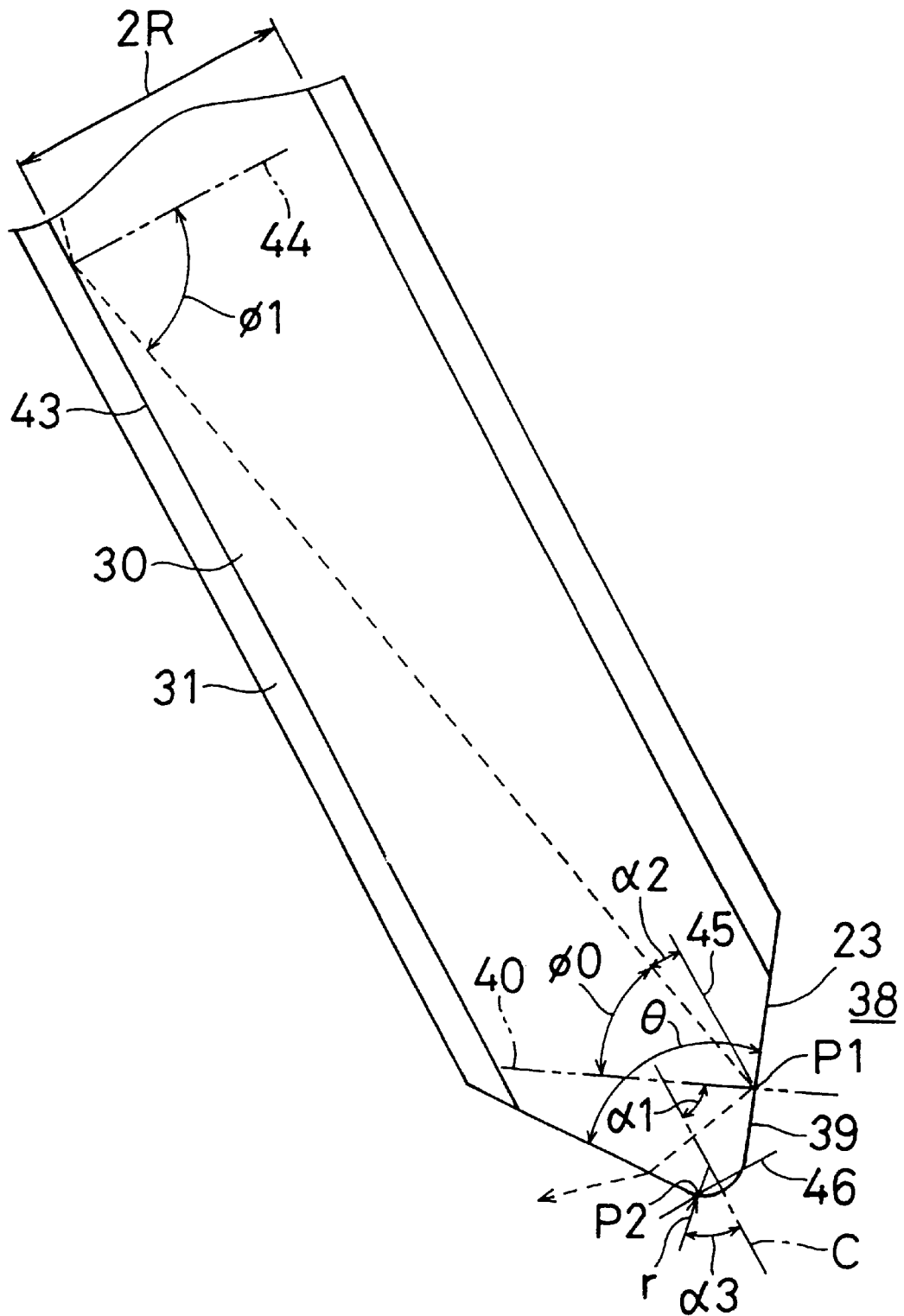
FIG. 4 is an enlarged view schematically showing first and second emission faces 23 and 24 of a core of the emission fiber and vicinities of the faces.

FIG. 4 is an enlarged view schematically showing the vicinities of the first and second emission faces 23 and 24 of the core 30 of the emission fiber 12. As shown in FIG. 4, in order to laterally emit a laser beam from the first emission face 23, preferably, the laser beam is reflected one time by a boundary plane 39 between the core 30 and the external space 38 and in the first emission face 23, and then emitted at the position opposed to the reflecting point from the first emission face 23 to an external space 38. The laser beam which reaches the first emission face 23 is totally reflected by the boundary plane 39 under the conditions that the angle of incidence to the boundary plane 39 with respect to a normal 40 of the boundary plane 39 is not smaller than the critical angle φ0 [deg] of the boundary plane 39. The critical angle φ0 is given by $$\sin \phi 0 = n0/n1 \quad (1)$$

wherein n0 is the refractive index of the external space 38 and n1 is that of the core 30.

The laser beam which propagates in the core 30 reaches the first emission face 23 with being totally reflected by the boundary plane 43 between the core 30 and the clad 31. The laser beam is totally reflected by the boundary plane 43 under the conditions that the angle of incidence to the boundary plane 43 with respect to a normal 44 of the boundary plane 43 is not smaller than the critical angle φ1 [deg.] of the boundary plane 43. The critical angle φ1 is given by $$\sin \phi 1 = n2/n1 \quad (2)$$

wherein n2 is the refractive index of the clad 31.

In the laser beam which reaches the first emission face 23, the laser beam which enters the boundary plane 39 at the smallest angle with respect to the normal 40 is a laser beam which propagates with being reflected by the boundary plane 43 between the core 30 and the clad 31 at the smallest angle with respect to the normal 44 of the boundary plane 43, and then reaches the first emission face 23, i.e., a laser beam which propagates with being reflected by the boundary plane 43 at the critical angle φ1 and then reaches the first emission face 23. From the above, it will be noted that a laser beam which propagates with being reflected by the boundary plane 43 at the critical angle φ1 to reach the first emission face art 23 and enter the boundary plane 39 is totally reflected one time by the boundary plane 39.

When a laser beam is reflected by the boundary plane 43 at the critical angle φ1 and then by the boundary plane 39 at the critical angle φ0, the apex angle θ [deg] of the first emission face 23 is given by an expression below.

$$\phi 1 - \theta/2 = \phi 0 \quad (3)$$

More specifically, since the sum of the interior angles of a triangle is 180 degrees, the angle α1 [deg] formed by the optical axis C and the normal 40 is expressed by an expression below.

$$\alpha 1 = 90 - \theta/2 \quad (4)$$

Furthermore, since the sum of the interior angles of a triangle is 180 degrees, the angle α2 [deg] formed by a line 45 which is parallel with the optical axis C and passes through the incidence point P1 of the laser beam to the boundary plane 39, and the laser beam is expressed as follows.

$$\alpha 2 = 90 - \phi 1 \quad (5)$$

Since the alternate interior angles are equal to each other, the following expression is attained.

$$\alpha 1 = \phi 0 + \alpha 2 \quad (6)$$

From expressions (4) to (6), expression (3) is attained. Therefore, when the apex angle of the first emission face 23 is selected not to be larger than the apex angle θ satisfying expression (3), a laser beam which reaches the first emission face 23 can be totally reflected one time by the boundary plane 39. As a result, the laser beam can be laterally emitted from the first emission face 23 to, for example, the region A1. The conditions under which a laser beam reaching the first emission face 23 is totally transmitted through the face, i.e., those under which the laser beam is not laterally emitted in a ring-like shape result in the conditions under which light which is most hardly transmitted in the laser beam reaching the first emission face 23, i.e., light which is nearly parallel with the optical axis C is transmitted through the face. When the conditions are satisfied, light propagating in the emission fiber 12 is not laterally emitted in a ring-like shape and is totally transmitted so as to be emitted along the optical axis C.

Assuming that the external space 38 is filled with air, the core 30 is made of quartz, and the clad 31 is made of F (fluorine)-added quartz, n0 is 1, n1 is 1.458, n2 is 1.443, the critical angle φ0 is 43.30 degrees, and the critical angle φ1 is 81.77 degrees. At this time, the apex angle θ is 76.94 degrees. When the apex angle of the first emission face 23 is selected not to be larger than 76.94 degrees, a laser beam which reaches the first emission face 23 can be totally reflected one time by the boundary plane 39 so as to be laterally emitted. When the apex angle of the first emission face 23 is selected not to be smaller than 93.4 degrees, a laser beam which reaches the first emission face 23 can be totally transmitted through the face. In this case, the laser beam is not laterally emitted in a ring-like shape from the first emission face 23 but emitted from the first emission face 23 in the direction of the optical axis C, with the result that irradiation is conducted only toward the front of the emission fiber 12.

When the external space 38 is filled with water, n0 is 1.33 and the critical angle φ0 is 65.81 degrees. At this time, the apex angle θ is 31.92 degrees. When the apex angle of the first emission face 23 is selected not to be larger than 31.92 degrees, a laser beam which reaches the first emission face 23 can be totally reflected one time by the boundary plane 39 so as to be laterally emitted.

As described above, the second emission face 24 is spherical, and a virtual sphere including the second emission face 24 is formed so as to be tangent to the first emission face 23 over the whole periphery with respect to the optical axis C. In other words, on a virtual plane including the optical axis C, the tangent of the second emission face 24 at a boundary point P2 between the first and second emission faces 23 and 24 coincides with the first emission face 23. The area S1 of the core 30 in a section 46 which includes the boundary line between the first and second emission faces 23 and 24 and which is perpendicular to the optical axis C is given by $$S1 = \pi \times (r \times \sin \alpha 3) \quad (7)$$

wherein r is the radius of curvature of the second emission face 24 and α3 is the angle [deg] formed by the optical axis C and the normal which passes through the boundary point P2 and which is perpendicular to the second emission face 24. Since the sum of the interior angles of a triangle is 180 degrees, the angle $\alpha 3$ is given by an expression below.

$$\alpha 3 = 90 - \theta/2 \tag{8}$$

When it is assumed that the laser beam which is guided with propagating in the core 30 of the emission fiber 12 shows a uniform intensity distribution, the intensity ratio of the laser beam which reaches the second emission face 24 and is then emitted through the second emission face 24 to the external space 38, to the whole of the laser beam is considered to be nearly equal to the sectional area ratio S1/S0 of the area Si of the section including the boundary line of the first and second emission faces 23 and 24 to the sectional area S0 of the whole of the core 30. When the radius of the core 30 is indicated by R, the sectional area S0 of the whole of the core 30 is expressed as follows.

$$S0 = \pi \times R^2 \tag{9}$$

Consequently, the sectional area ratio S1/S0 is expressed as follows.

$$S1/S0 = (r \times \sin \alpha 3)^2 / R^2 \tag{10}$$

Therefore, the intensity ratio of the laser beam emitted through the second emission face 24 can be changed depending on the radius of curvature r of the second emission face 24. In accordance with the site to be treated, the frequencies of the laser beams emitted through the first and second emission faces 23 and 24 which contribute to the evaporation of the dentin, or the like, the radius of curvature r of the second emission face 24 is selected, and the intensity ratio of the laser beams emitted through the first and second emission faces 23 and 24 is selected, so that the workability is improved.

In the root canal preparation, for example, the laser beam emitted through the second emission face 24 is required only at the root apex. Therefore, the intensity of the laser beam emitted through the second emission face 24 is selected to be in the range of 1 to 20%, preferably, 5 to 15% of that of the whole laser beam entering the incidence end. By contrast, the intensity of the laser beam which is radially emitted in a ring-like shape through the first emission face 23 is selected to be in the range of 80 to 99%, preferably, 85 to 95% of that of the whole laser beam entering the incidence end. In this way, the first laser beam which is axially emitted, and the second laser beam which is radially emitted in a ring-like shape are different in intensity from each other. However, the first laser beam emitted through the second emission face 24 is converged forward to the optical axis C, and hence a high energy can be obtained in the vicinity of the optical axis. Therefore, the energy density of the first laser beam can be made nearly equal to that of the second laser beam. As a result, the dentin in front of and at the side of the emission end portion 22 of the emission fiber 12 can be evaporated in a nearly uniform manner.

Figure 5:
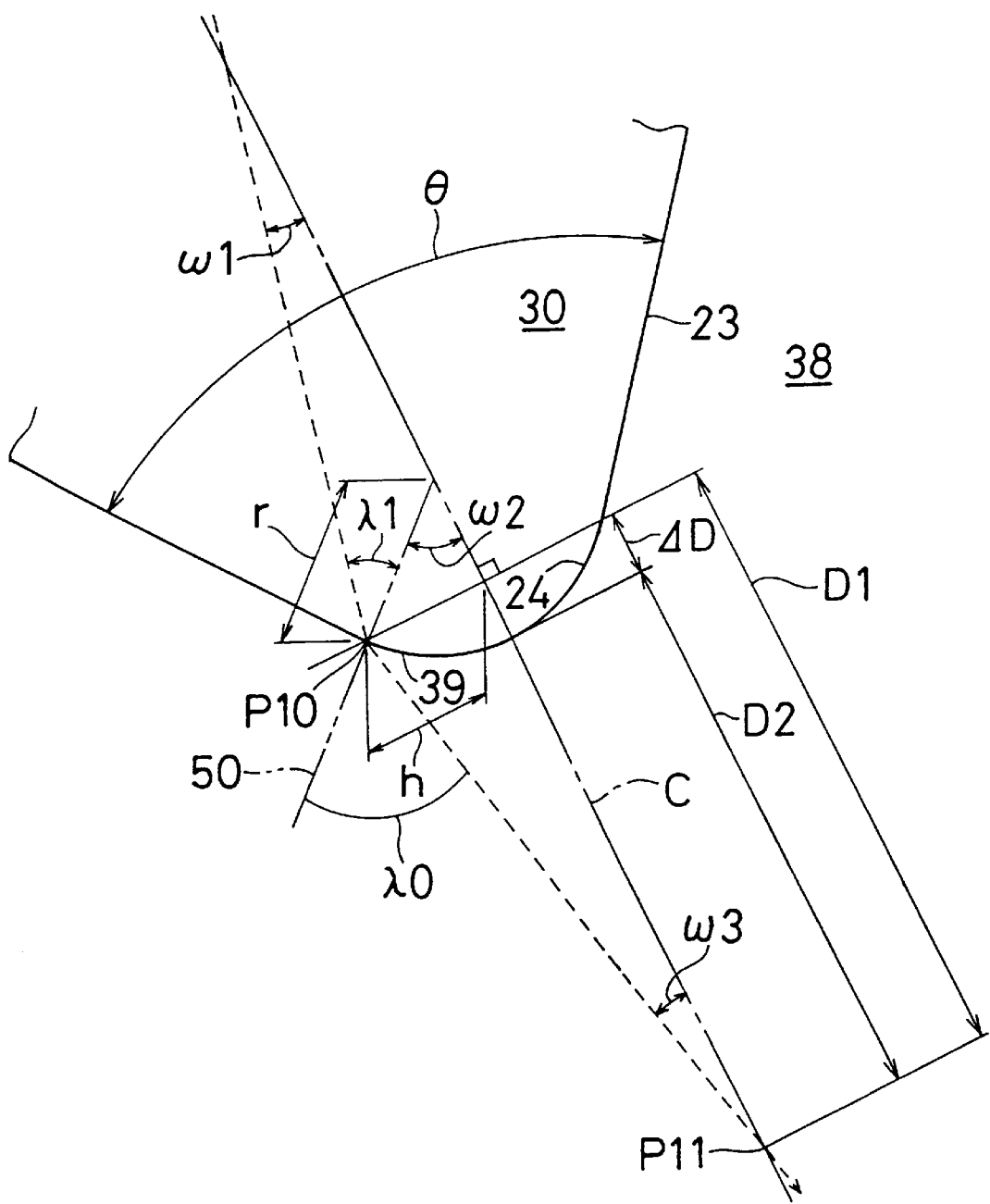
FIG. 5 is an enlarged view schematically showing the second emission face 24 of the core of the emission fiber and a vicinity of the face.

FIG. 5 is an enlarged view schematically showing the vicinity of the second emission face 24 of the core 30 of the emission fiber 12. Referring to FIG. 5, the convergence of the laser beam emitted through the second emission face 24 will be considered. When a laser beam enters the boundary plane 39 between the core 30 and the external space 38 in the second emission face 24 at an angle $\omega 1$ [rad] with respect to the optical axis C, the angle $\omega 2$ [rad] formed by the optical axis C and the normal 50 of the second emission face 24 which passes through the point of incidence P10 of the laser beam to the boundary plane 39 is given by $$\omega 2 = \sin^{-1}(h/r) \tag{11}$$

wherein h is the distance between the point of incidence P10 and the optical axis C in the direction perpendicular to the optical axis C. The angle $\omega 3$ [rad] formed by the optical axis C and the laser beam which is refracted at the boundary plane 39 and emitted through the second emission face 24 is given by $$\omega 3 = \tan^{-1}(h/D1) \tag{12}$$

wherein D1 is the distance between the point of incidence P10 and the point of intersection P11 of the emitted laser beam and the optical axis C, in the direction parallel to the optical axis C.

Since the sum of the interior angles of a triangle is 180 degrees, the angle of incidence $\lambda 1$ [rad] and the angle of emission $\lambda 0$ [rad] of the laser beam at the boundary plane 39 with respect to the normal 50 are obtained by expressions below.

$$\lambda 1 = \omega 2 - \omega 1 \tag{13}$$

$$\lambda 0 = \omega 2 + \omega 3 \tag{14}$$

Since $\sin \lambda 1 \times n1 = \sin \lambda 0 \times n0$, the following is attained $$\lambda 0 = \sin^{-1}\{(n1/n0) \times \sin \lambda 1\} \tag{15}$$

From expressions (13) to (15), $\omega 3$ is given by an expression below.

$$\omega 3 = \lambda 0 - \omega 2 = \sin^{-1}\{(n1/n0) \times \sin \lambda 1\} - \omega 2 = \sin^{-1}\{(n1/n0) \times \sin(\omega 2 - \omega 1)\} - \omega 2 \tag{16}$$

From expressions (11), (12), and (16), the distance D1 is given by $$D1 = \frac{(r \times \sin \omega 2)}{\tan\left[\sin^{-1}\left\{\frac{n1}{n0} \times \sin(\omega 2 - \omega 1)\right\} - \omega 2\right]} \tag{17}$$

wherein the angles $\omega 1$, $\omega 2$, and $\omega 3$ are expressed in radian.

When the point of incidence P10 of the laser beam to the boundary plane 39 coincides with the boundary point between the first and second emission faces 23 and 24, the angles $\omega 2$ and $\omega 1$ are expressed as follows.

$$\omega 2 = \alpha 3 \tag{18}$$

$$\omega 3 = \alpha 2 \tag{19}$$

As a result, the angle $\omega 2$ is an apex angle at which the laser beam is totally reflected one time by the first emission face 23, and the following relationship is held with respect to the largest apex angle $\theta$ of the first emission face 23.

$$\omega 2 = (\pi/180) \times \{90 - (\theta/2)\} \tag{20}$$

Assuming that the laser beam propagates with being reflected by the boundary plane 43 between the core 30 and the clad 31 at the critical angle $\phi 1$, the angle $\omega 1$ is expressed as follows.

$$\omega 1 = (\pi/180) \times (90 - \phi 1) \tag{21}$$

Therefore, the distance D1 is given by an expression below.

$$D1 = \frac{r \times \sin\left\{\frac{\pi}{180} \times \left(90 - \frac{\theta}{2}\right)\right\}}{\tan\left[\sin^{-1}\left\{\left(\frac{n1}{n0}\right) \times \sin\left[\left\{\frac{\pi}{180} \times \left(90 - \frac{\theta}{2}\right)\right\} - \left\{\frac{\pi}{180} \times (90 - \psi 1)\right\}\right]\right\} - \left\{\frac{\pi}{180} \times \left(90 - \frac{\theta}{2}\right)\right\}\right]} \quad (22)$$

Furthermore, the distance ΔD between the point of incidence P10 and the tip end of the second emission face 24 in the parallel direction of the optical axis C is expressed as follows.

$$\Delta D = r - (r \times \cos \omega 2) \quad (23)$$

The distance D2 between the tip end of the second emission face 24 and the point of intersection P11 is expressed as follows.

$$D2 = D1 - \Delta D \quad (24)$$

From the above, when the external space 38 is filled with air and the apex angle θ of the first emission face 23 is 76.94 degrees, the following is held.

$$D2 = 1.010r - 0.622r = 0.388r \quad (25)$$

When the external space 38 is filled with water and the apex angle θ of the first emission face 23 is 31.92 degrees, the following is held.

$$D2 = 3.653r - 0.274r = 3.379r \quad (26)$$

In this way, br example, the distance D2 between the tip end of the second emission face 24 and the focal point P11 can be expressed by using the radius of curvature r of the second emission face 24.

Figure 6:
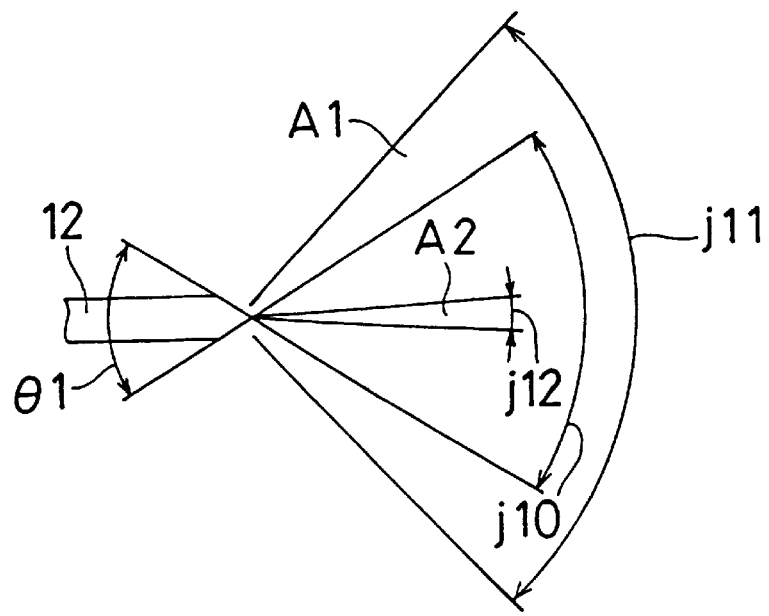
FIG. 6 is a diagram showing an emission range of an emitted laser beam in the case of the emission end portion of the emission fiber having an apex of 60 degrees.

FIG. 6 is a diagram showing an emission pattern obtained in the case where the diameter of the core is 600 μm, the apex angle θ1 of the first emission face 23 is 60 degrees, and the radius of curvature r of the second emission face 24 is 30 μm. When the first and second emission faces 23 and 24 are formed as described above, the second laser beam is emitted from the first emission face 23 to the region A1 in which the illumination shape is annular and which exists between the innermost spread angle j10 of 64 degrees and the outermost spread angle j11 of 92 degrees, and the first laser beam is emitted from the second emission face 24 to the region A2 which is nearly circular and in which the spread angle j12 is 7 degrees.

Figure 7:
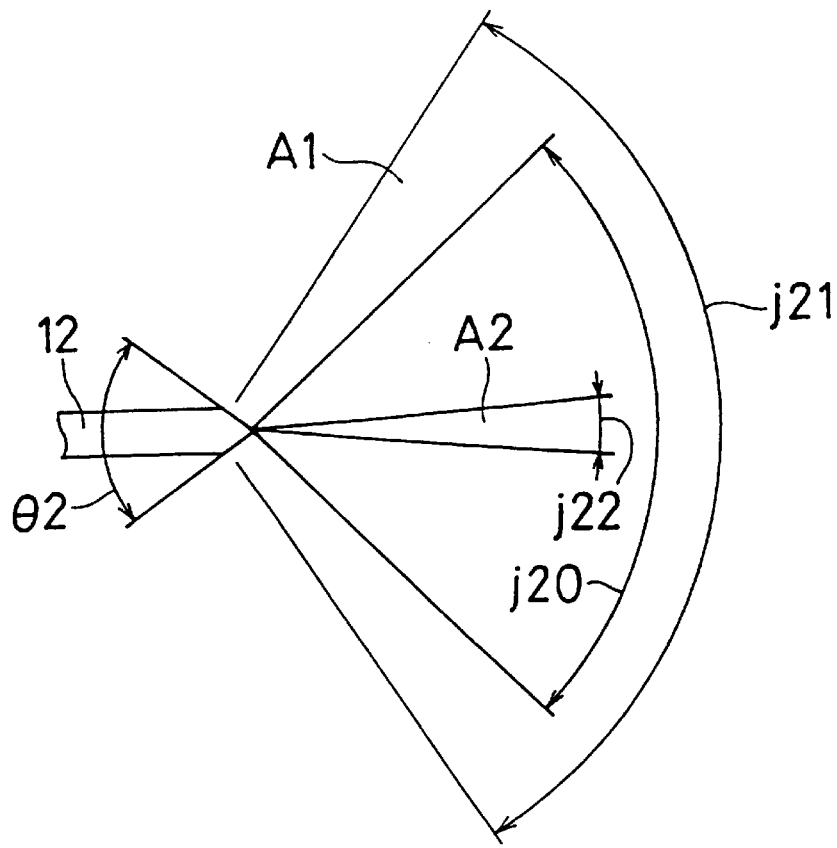
FIG. 7 is a diagram showing an emission range of an emitted laser beam in the case of the emission end portion of the emission fiber having an apex of 70 degrees.

FIG. 7 is a diagram showing an emission pattern obtained in the case where the diameter of the core is 600 μm, the apex angle θ2 of the first emission face 23 is 70 degrees, and the radius of curvature r of the second emission face 24 is 30 μm. When the first and second emission faces 23 and 24 are formed as described above, the second laser beam is emitted from the first emission face 23 to the region A1 in which the illumination shape is annular and which exists between the innermost spread angle j20 of 84 degrees and the outermost spread angle j21 of 111 degrees, and the first laser beam is emitted from the second emission face 24 to the region A2 which is nearly circular and in which the spread angle j22 is 8 degrees.

Figure 8:
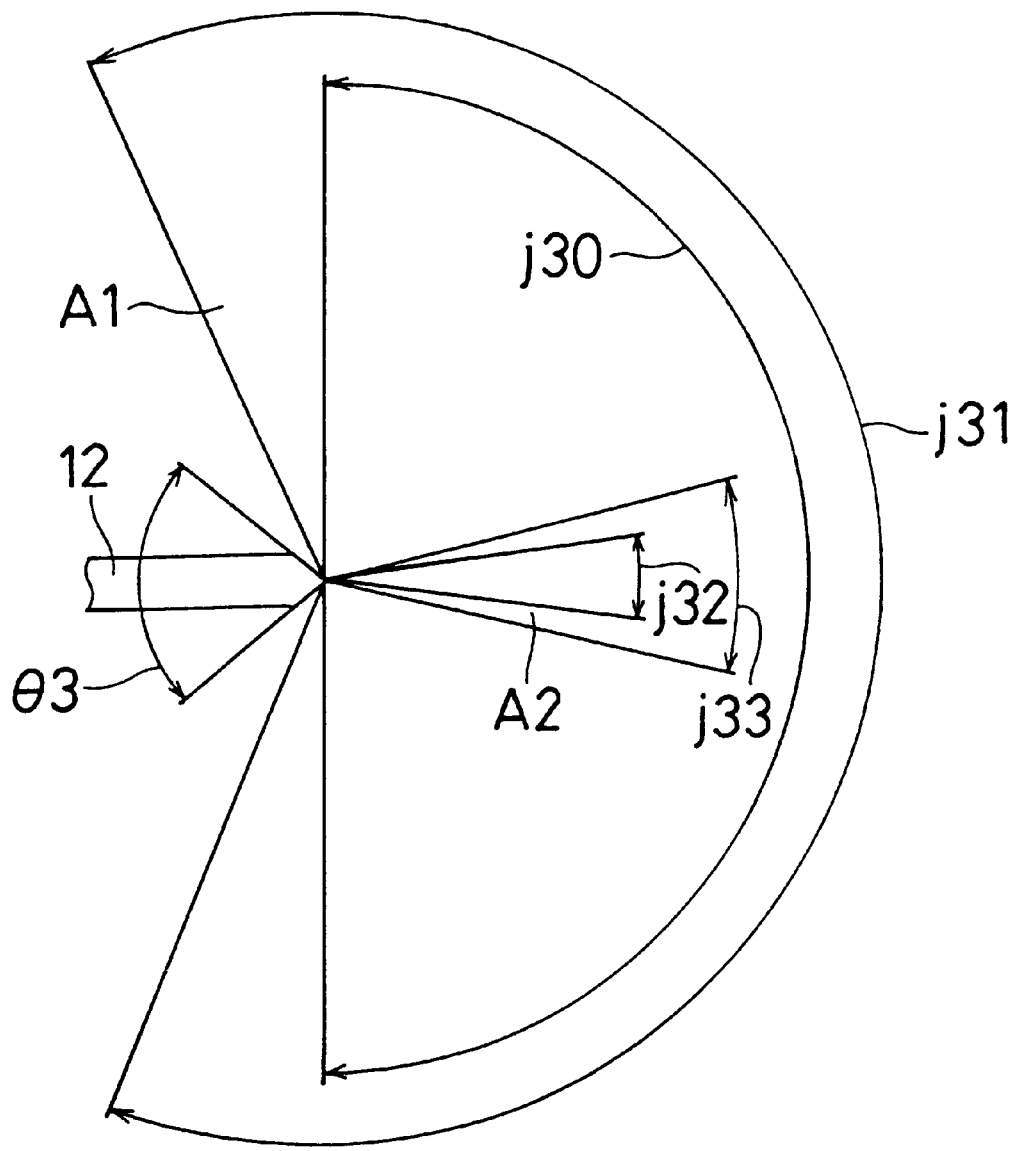
FIG. 8 is a diagram showing an emission range of an emitted laser beam in the case of the emission end portion of the emission fiber having an apex of 80 degrees.

FIG. 8 is a diagram showing an emission pattern obtained in the case where the diameter of the core is 600 μm, the apex angle θ3 of the first emission face 23 is 80 degrees, and the radius of curvature r of the second emission face 24 is 30 μm. When the first and second emission faces 23 and 24 are formed as described above, the second laser beam is emitted from the first emission face 23 to the region A1 in which the illumination shape is annular and which exists between the innermost spread angle j30 of 180 degrees and the outermost spread angle j31 of 227 degrees, and the first laser beam is emitted from the second emission face 24 to the region A2 in which the illumination shape is annular and which exists between the innermost spread angle j32 of 15 degrees and the outermost spread angle j33 of 26 degrees.

Figure 9:
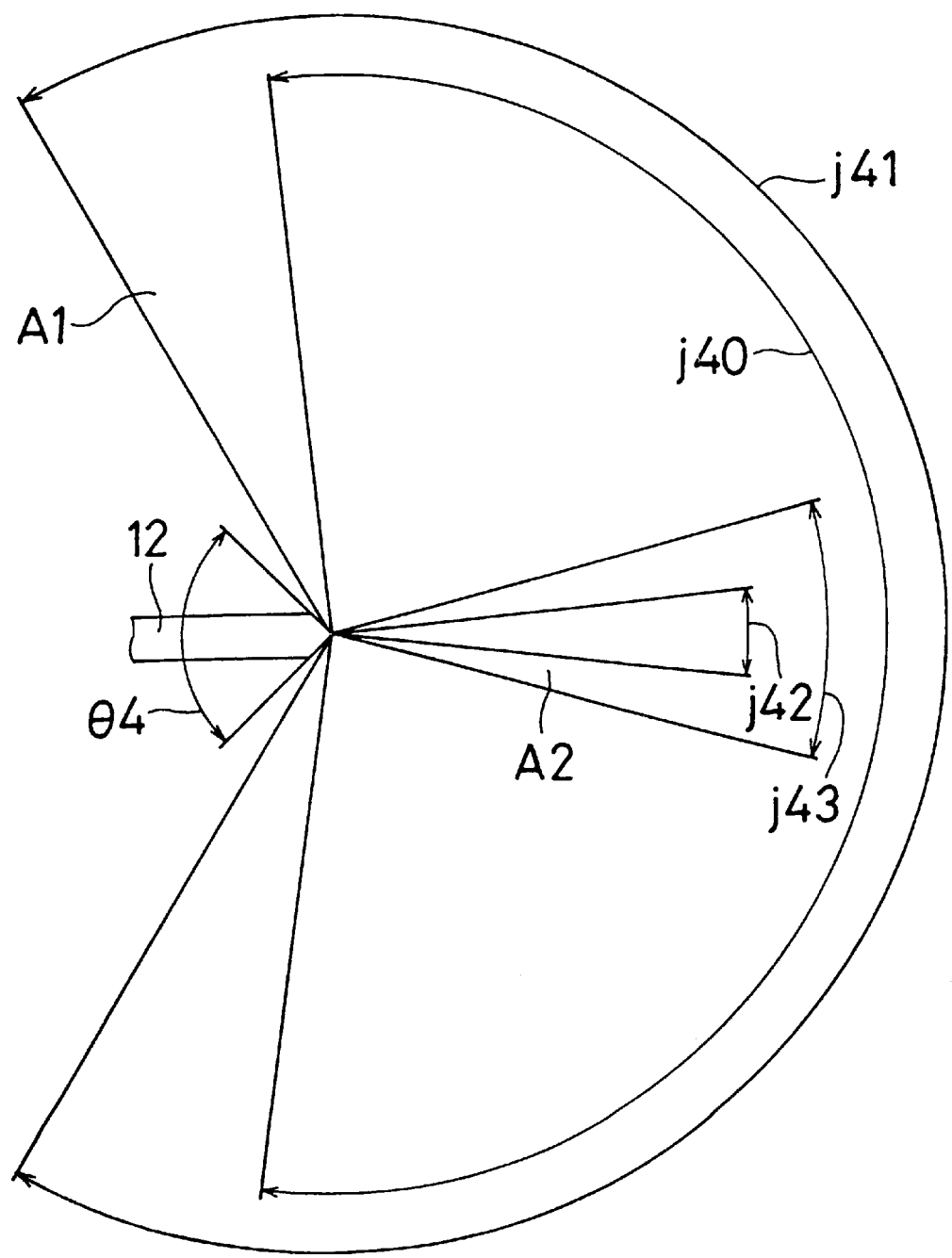
FIG. 9 is a diagram showing an emission range of an emitted laser beam in the case of the emission end portion of the emission fiber having an apex of 90 degrees.

FIG. 9 is a diagram showing an emission pattern obtained in the case where the diameter of the core is 600 μm, the apex angle θ4 of the first emission face 23 is 90 degrees, and the radius of curvature r of the second emission face 24 is 30 μm. When the first and second emission faces 23 and 24 are formed as described above, the second laser beam is emitted from the first emission face 23 to the region A1 in which the illumination shape is annular and which exists between the innermost spread angle j40 of 194 degrees and the outermost spread angle j41 of 240 degrees, and the first laser beam is emitted from the second emission face 24 to the region A2 in which the illumination shape is annular and which exists between the innermost spread angle j42 of 12 degrees and the outermost spread angle j43 of 29 degrees.

Figure 10:
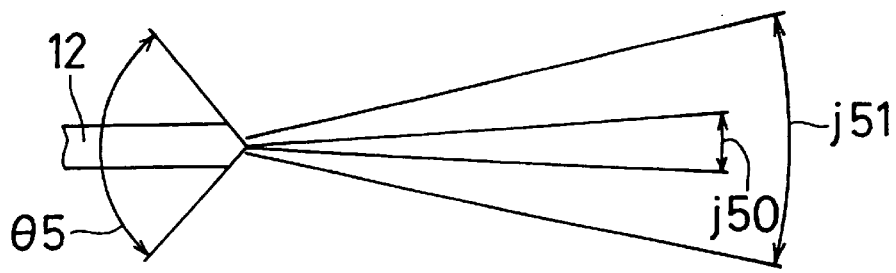
FIG. 10 is a diagram showing an emission range of an emitted laser beam in the case of the emission end portion of the emission fiber having an apex of 100 degrees.

FIG. 10 is a diagram showing an emission pattern obtained in the case where the diameter of the core is 600 μm, the apex angle θ5 of the first emission face 23 is 100 degrees, and the radius of curvature r of the second emission face 24 is 30 θm. When the first and second emission faces 23 and 24 are formed as described above, single light is emitted forward from the first and second emission faces 23 and 24 to the region A1 in which the illumination shape is annular and which exists between the innermost spread angle j50 of 10 degrees and the outermost spread angle j51 of 25 degrees. In this way, when the apex angle of the first emission face 23 is larger than 93.4 degrees, the second laser beam is not substantially emitted laterally and radially from the emission end portion 22 of the emission fiber 12, and light is emitted only forward from the emission end portion 22 in the axial direction of the emission fiber 12.

Figure 11:
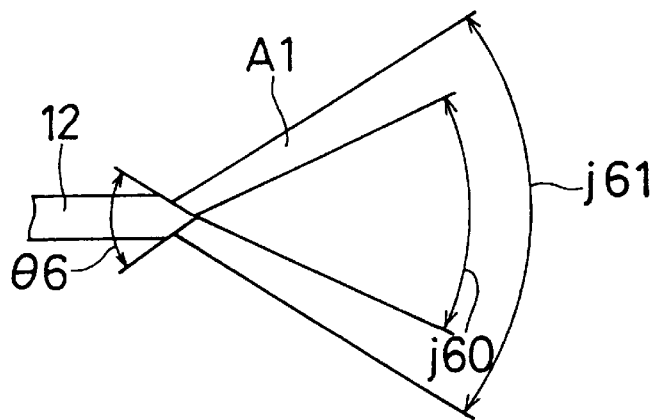
FIG. 11 is a diagram showing an emission range of an emitted laser beam in the case of the emission end portion of the emission fiber having an apex of 54 degrees.

FIG. 11 is a diagram showing an emission pattern obtained in the case where the diameter of the core is 600 μm, the apex angle θ6 of the first emission face 23 is 54 degrees, and the radius of curvature r of the second emission face 24 is 30 μm. When the first and second emission faces 23 and 24 are formed as described above, single light is emitted forward from the first and second emission faces 23 and 24 to the region A1 in which the illumination shape is annular and which exists between the innermost spread angle j60 of 45 degrees and the outermost spread angle j61 of 60 degrees. In this way, when the apex angle of the first emission face 23 is smaller than 60 degrees, the amount of light which is emitted forward from the emission end portion 22 of the emission fiber 12 is extremely reduced, and light is emitted from the emission end portion 22, only in a direction which is oriented diagonally forward with respect to the radial direction of the emission fiber 12.

In the case where the diameter of the core of the emission fiber 12 is about 200 to 600 μm, the emission patterns similar to those shown in FIGS. 6 to 11 are obtained for the same apex angles when the radius of curvature r of the second emission face 24 is in the range of 5 to 100 μm.

As described above, when the apex angle of the first emission face 23 of the emission fiber 12 is set to be 60 to 93 degrees, a laser beam entering the incidence end is emitted partially as a first laser beam forward from the emission end portion in the axial direction, and partially as a second laser beam in a ring-like shape laterally from the emission end portion in the radial direction. When the first laser beam to be forward emitted and the second laser beam to be laterally emitted are positively used as beams for a laser treatment as described later in detail, therefore, these beams can be applied particularly to the field of the dental treatment, for example, sterilization of a root canal, evaporation of a dental pulp, treatment of a root apex, and a fissure sealant. When the apex angle is set to be 60 to 90 degrees, the second laser beam from the emission end portion 22 of the emission fiber 12 is radially emitted in the range of about 45 to 90 degrees with respect to the axis as shown in FIGS. 6 to 9. In the root canal preparation, for example, the dentin of the root canal wall and the dental pulp over the whole periphery of the root canal can be evaporated. When the apex angle is set to be 70 to 90 degrees, particularly, the second laser beam is emitted in a nearly perpendicular direction, thereby enabling a laser beam to enter also dental canaliculi which are formed in a direction perpendicular to the root canal wall. Therefore, also sterilization of infected root canals can be completely conducted. In the case where a reamer processing is performed before a laser treatment, the apex angle is preferably set to be 70 to 80 degrees. As a result of this setting, the apex angle is nearly equal to the point angle of a reamer used in the reamer processing, so that also the tip end portion of the reamer processing can e irradiated with the laser beam. Moreover, when the apex angle is set to be 80 to 90 degrees, the first laser beam from the emission end portion 22 is emitted in a ring-like shape in the axial direction, and hence the first laser beam irradiates with being spread at a certain angle. In the root canal preparation, for example, the whole periphery of the tip end of the reamer can be irradiated with a laser beam.

Figure 12:
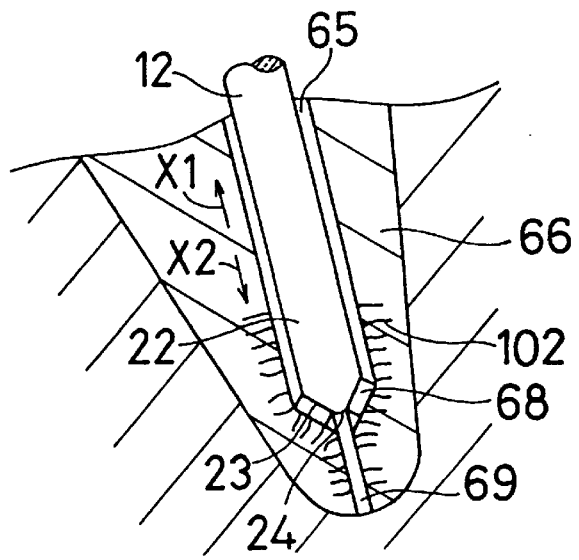
FIG. 12 is a section view showing a state where the emission fiber is inserted into a root canal 65.

The laser treatment apparatus 60 comprising the laser handpiece 63 to which the probe 10 is attached can be used in a dental treatment in the following manner. For example, the laser handpiece 63 is held by the operator, the emission fiber 12 of the probe 10 is inserted into a root canal 65 as shown in FIG. 12, and a root canal wall 66 facing the root canal 65 is irradiated with a laser beam, thereby evaporating the dentin of the root canal wall 66. Dental canaliculi 102 elongate in the root canal wall in a perpendicular direction. Also the dental canaliculi 102 can be irradiated with the laser beam so that also sterilization of infected root canals can be conducted. When the probe 10 is used in a dental treatment, the first laser beam can be emitted forward with respect to the emission end portion 22 of the emission fiber 12 and the second laser beam can be emitted laterally with respect to the emission end portion 22, and the dentin of the irradiated site can be evaporated by the first and second laser beams. When the probe 10 is used for evaporating the dentin of the root canal 65, the root canal insertion length, i.e., the projection distance L of the emission end portion 22 is set to be, for example, 3 mm or more, and about 3 to 25 mm in general. In the case of a treatment of the root canal, for example, the projection distance is selected to be about 15 to 20 mm. Therefore, the emission end portion 22 can be sufficiently inserted to the vicinity of a root apex 68, so that the treatment of the root canal can be preferably conducted. The emission fiber 12 is elastically deformable. Even when the root canal 65 is arcuate, for example, the emission fiber can be inserted to the root apex 68 along the shape of the root canal. In order to facilitate the insertion of the emission fiber 12, a prepared hole may be formed in advance by using a small reamer.

In the above-mentioned root canal preparation, the laser beam irradiation from the root canal orifice is restricted in the evaporable range because the root canal 65 is narrow, and hence the emission fiber 12 of the probe 10 must be inserted into the root canal 65 so as to evaporate the dentin of the root canal wall 66. In the probe 10, the laser beam can be laterally emitted uniformly as the second laser beam from the first emission face 23 of the emission fiber 12. Therefore, the emission fiber 12 can be inserted from the root canal orifice and the laser beam is emitted while the fiber is moved in the directions X1 and X2 along which the root canal 65 elongates, whereby the dentin of the root canal wall 66 can be evaporated over the whole periphery of the root canal 65 and in the range from the root canal orifice to the vicinity of the root apex 68. Furthermore, since the laser beam can be forward emitted as the first laser beam also through the second emission face 24, the dentin of the root canal wall 66 can be evaporated also at the root apex 68. In this way, also in the treatment of the root canal wall 66 facing in the narrow root canal 65 in which the direction of the emission end portion 22 of the emission fiber 12 cannot be easily selected, the treatment can be conducted as required by inserting the emission fiber 12 into the root canal 65.

When the emission fiber 12 in which, as shown in FIGS. 8 and 9, the emission direction of the region A1 emitted radially from the first emission face 23 is oriented more rearward than the emission end portion 22 is used, evaporation dust of the dentin and dental pulp tissues produced by the laser beam irradiation can be ejected from the root canal orifice to the outside by moving the emission end portion 22 in such a manner that the emission end portion is pulled up from the root apex portion toward the root canal orifice. When a combination of laser beam irradiation and water supply is used, the laser beam is absorbed to the water in a root canal so that the cavitation effect is produced there. As a result, also removal of evaporation dust and cleaning can be conducted in the root canal.

When a dental treatment is conducted by using a laser beam in this way, the dentin can be evaporated so as to remove the source of infection and the like, and also the sterilization process can be conducted. Also at the root apex, the evaporation of the dentin and the sterilization process can be preferably conducted. Moreover, when a treatment is conducted by using a laser beam in this way, it is possible to prevent apical periodontitis and the like from occurring.

The conventional reamer processing on a root apex may accurately form a hole in the root apex. When such a hole is formed, various disorders such as inflammation may be occurred. By contrast, in the laser irradiation treatment, even if a hole is formed in the root apex by a laser beam, only a thin portion of the surface layer of the hole-formed portion of the root apex is modified and evaporated under a sterilized state, and damages such as scraping the tissues by a reamer or the like are not produced. Also in this view point, therefore, the laser irradiation treatment is very safer.

The first emission face 23 of the emission end portion 22 of the emission fiber 12 is formed into a circular conical shape. According to this configuration, a laser beam can be emitted from the first emission face 23 peripherally and laterally with respect the optical axis C with a uniform or nearly uniform intensity distribution. Therefore, portions of the dentin which are separated from the emission end portion 22 of the emission fiber 12 by a nearly same distance can be evaporated by a uniform or nearly uniform thickness. For example, since the dentin facing a nearly cylindrical space can be evaporated by a nearly uniform thickness, the laser handpiece can be preferably used.

As described above, the formation of the second emission face 24 into a spherical shape allows the laser beam to be emitted from the second emission face 24 with being converged. Therefore, even when the intensity ratio of the laser beam emitted from the second emission face 24 is small as described above, the intensity in the irradiation site can be increased. In the root canal preparation, for example, the intensity ratio of the laser beam which is required mainly for evaporating the dentin facing the root apex 68 is made small so that the laser beam is effectively used and a rapid and effective treatment is conducted, and the laser beam can be emitted also in the forward direction at a sufficient intensity. Furthermore, the convergence can reduce the diameter of the light flux, so that the dentin facing a space of a minute diameter such as a root apex hole 69 is satisfactorily evaporated. Moreover, the formation of the second emission face 24 into a spherical shape prevents soft tissues of the patient from being damaged even when the tip end of the emission fiber 12 is contacted with the soft tissues. The emission fiber 12 can be easily moved under a state where the tip end of the emission fiber 12 is contacted with hard soft tissues of the patient.

The electrode 34 which is made of an electrically conductive material is disposed on the periphery of the emission fiber 12. The electrode 34 may be used as an electrode for a root canal of a measuring instrument 71 which measures a current flowing between the electrode 34 and a contact terminal paired with the electrode to obtain the electric resistance between the paired electrodes, and measures the root canal length based on the electric resistance. As shown in FIG. 1, the other electrode or an oral electrode 70 which is separately prepared is contacted with a predetermined site of the mouth, for example, the lip, and the emission fiber 12 is inserted into the root canal 65. Then, the resistance of the portion extending between the root canal electrode 34 and the oral electrode 70 via the root apex 68 is measured, whereby the position of the emission end portion 22 of the emission fiber 12 in the root canal 65 can be detected. Therefore, the dentin of the site to be evaporated can be evaporated in a proper amount, and the treatment can be conducted rapidly, easily, and accurately. The root canal electrode 34 is disposed on the whole periphery of the emission fiber 12. In this case, the electrically conductive state of the tissues in the mouth between the root canal electrode 34 and the oral electrode 70 can be easily obtained. Therefore, the treatment can be conducted while easily detecting the position of the emission end portion 22 of the emission fiber 12.

Figure 13:
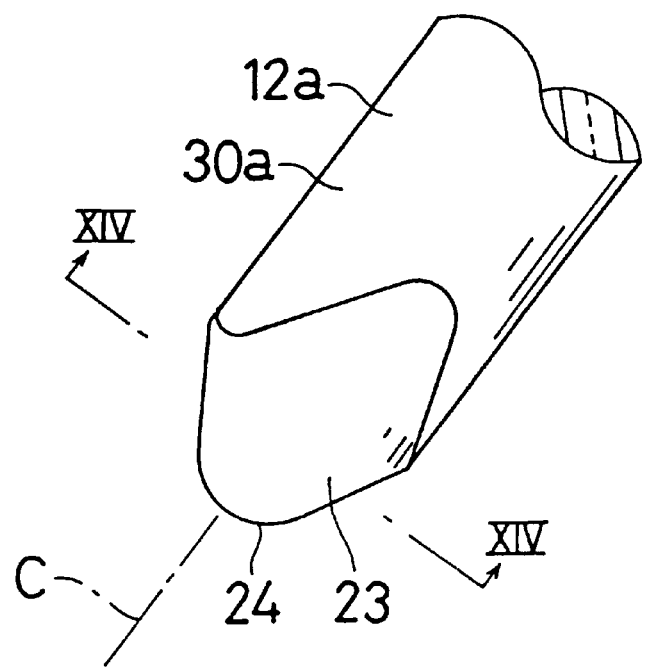
FIG. 13 is a perspective view showing the core of an emission fiber in another embodiment.
Figure 14:
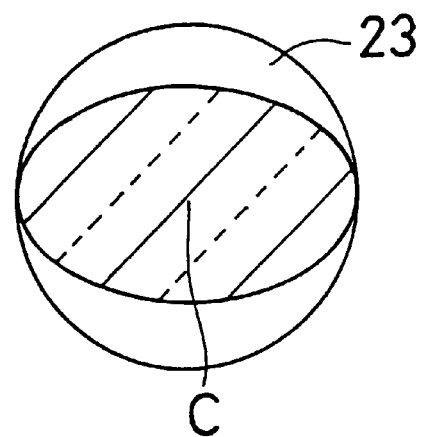
FIG. 14 is a sectional view taken on line XIV—XIV of FIG. 13.

FIG. 13 is a perspective view schematically showing a core 30a of an emission fiber 12a in another embodiment of the invention, and FIG. 14 is a sectional view taken along the section line XIV—XIV of FIG. 13. The components corresponding to those of the embodiment described above are designated with the same reference numerals and their description is omitted. Hereinafter, only different components will be described. In the embodiment, the first emission face 23 of the core 30a of the emission fiber 12a is formed into an elliptical conical shape in which a section perpendicular to the optical axis C has an elliptic shape. According to this configuration, the second laser beam which is laterally emitted in a ring-like shape is emitted from the first emission face 23 and with an uneven intensity distribution in which the intensity is changed at intervals of about 90 degrees in a peripheral direction with respect to the optical axis C. In FIG. 14, for example, the laser beam can be emitted with an intensity distribution in which the intensity is relatively high in the vertical directions and relatively low in the lateral directions. Therefore, the dentin of sites separated from the emission end portion 22 of the emission fiber 12a by a distance which is changed at intervals of about 90 degrees can be evaporated by a uniform or nearly uniform thickness. For example, since the dentin facing a nearly elliptical cylindrical space such as the root canal 65 can be evaporated by a nearly uniform thickness, the laser handpiece can be preferably used.

Figure 15:
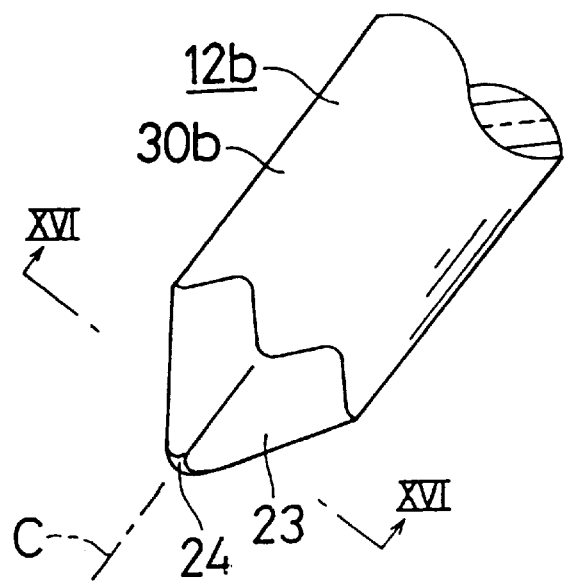
FIG. 15 is a perspective view showing a core of an emission fiber in a still another embodiment.
Figure 16:
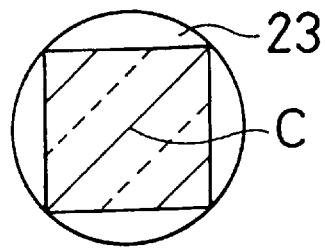
FIG. 16 is a section view taken on line XVI—XVI of FIG. 15.

FIG. 15 is a perspective view schematically showing a core 30b of an emission fiber 12b in a still another embodiment of the invention, and FIG. 16 is a section view taken along the section line XVI—XVI of FIG. 15. The components corresponding to those of the embodiment described above are designated with the same reference numerals and their description is omitted. Hereinafter, only different components will be described. In the embodiment, the first emission face 23 of the core 30b of the emission fiber 12b is formed into a regular quadrangular pyramid shape in which a section perpendicular to the optical axis C has a square shape. According to this configuration, the second laser beam which is laterally emitted in a ring-like shape is emitted from the first emission face 23 and with an uneven intensity distribution in which the intensity is changed at intervals of about 45 degrees in a peripheral direction with respect to the optical axis C. In FIG. 16, for example, the laser beam can be emitted with an intensity distribution in which the intensity is relatively high in the vertical and lateral directions and relatively low in oblique directions that are angularly displaced from the vertical directions by about 45 degrees in clockwise and counterclockwise directions. Therefore, the dentin of sites separated from the emission end portion 22 of the emission fiber 12b by a distance which is changed at intervals of about 45 degrees can be evaporated by a uniform or nearly uniform thickness.

The first emission face 23 is not required to have a regular quadrangular pyramid shape, and may have another regular polygonal pyramid shape in which a section perpendicular to the optical axis C has a regular polygonal shape, or another polygonal pyramid shape in which a section perpendicular to the optical axis C has a distorted polygonal shape. In the case where the dentin of sites separated from the emission end portion 22 of the emission fiber 12b by a distance which is peripherally changed is to be evaporated, when the first emission face is selected so as to have an approximately polygonal pyramid shape corresponding to the change of the distance, the dentin of such sites can be evaporated by a uniform or nearly uniform thickness. In this way, in accordance with the shape of a space, the dentin facing the space can be evaporated by a uniform or nearly uniform thickness. Therefore, the laser handpiece can be preferably used.

Figure 17:
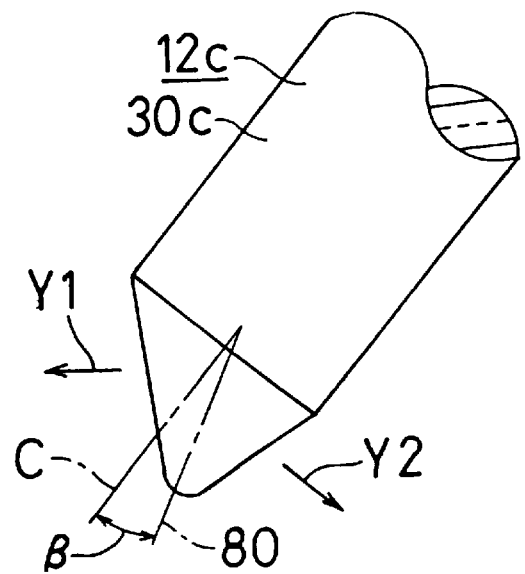
FIG. 17 is a perspective view showing a core of an emission fiber in a yet another embodiment.

FIG. 17 is a perspective view schematically showing a core 30c of an emission fiber 12c in a yet another embodiment of the invention. The components corresponding to those of the embodiment described above are designated with the same reference numerals and their description is omitted. Hereinafter, only different components will be described. In the embodiment, the first emission face 23 of the core 30c of the emission fiber 12c is formed into an eccentric circular conic shape which has an axis 80 forming an angle B to the optical axis C so that a section perpendicular to the axis 80 inclined with respect to the optical axis C has a circular shape. According to this configuration, second laser beam can be emitted peripherally with respect to the axis which is inclined to the optical axis C, for example, in lateral directions Y1 and Y2 shown in FIG. 17. Therefore, the dentin of a wall which is inclined so as to be separated from the axis of a space as moving from the inlet of the space to the tip end thereof can be easily evaporated.

The shape of the first emission face 23 which is eccentric from the optical axis C is not required to have a circular conical shape, and may have an eccentric elliptical conical shape in which a section perpendicular to the axis 80 is an elliptic shape, or an eccentric truncated regular polygonal pyramid shape in which a section perpendicular to the axis 80 has a regular polygonal shape. Furthermore, the first emission face may have another polygonal pyramid shape in which a section perpendicular to the axis 80 has a distorted polygonal shape. According to this configuration, the first emission face 23 can be formed into a tapered shape in accordance with a space which the site to be treated faces, and the dentin in such a site can be evaporated by a uniform or nearly uniform thickness in accordance with the shape of the space. Therefore, in accordance with the shape of a space, the dentin facing the space can be evaporated by an approximately uniform thickness, and hence the laser handpiece can be preferably used.

In addition to the shape of first emission face 23, also that of the second emission face 24 may be selected in accordance with the site to be treated. For example, the second emission face may have a flat shape which is perpendicular to the optical axis C, a flat shape which is inclined with respect to a plane perpendicular to the optical axis C, or another curved shape. The embodiments described above are only examples. The shapes of the first and second emission faces 23 and 24, the materials, structures, and dimensions of the emission fibers 12, 12*a*, 12*b*, and 12*c*, and the like may be adequately selected in accordance with the site to be treated. The laser is not restricted to Er-YAG laser, and HO-YAG (Holmium-Yttrium-Aluminum-Garnet) laser or the like may be used. When laser beam irradiation is conducted in a narrow space such as a pulp cavity, there may be a fear that the temperature rise in the pulp cavity produces a problem. Such a problem of the temperature rise can be solved by the use of Er-YAG laser because of the following reason. When tissues are irradiated by Er-YAG laser, the tissues are destroyed by the absorption and evaporation of a laser beam to $H_2O$ and OH groups. Therefore, the portion in which the temperature is raised by the absorption of the laser beam to the tissues are scattered together with destroyed chips, with the result that the amount of heat remaining in the tissue is reduced to a very low level. The temperature rise can be remarkably suppressed also by ejecting water only or a mixture of water and air in a spray form.

Alternatively, the emission fiber 12 may be an optical fiber in which an intermediate layer of a refractive index smaller than that of the clad 31 is formed between the core 30 and the clad 31, the core 30 has a refractive index distribution wherein the refractive index of a center portion is lower than that of the surrounding, the refractive index of the clad 31 is lower than that of the center portion of the core 30, and the refractive index is sharply changed at the boundary between the core 30 and the intermediate layer and that between the intermediate layer and the clad 31. When a laser beam enters the core 30 having a refractive index distribution wherein the refractive index of the center portion is lower than that of the surrounding, the energy density distribution of the emitted laser beam is nearly uniform in a radial direction of the core 30. Therefore, the energy density distribution of the laser beam emitted with being passed through the emission fiber 12 in the range corresponding to the whole face of the core 30 can be extremely uniformized. In the emission end portion 22 of the emission fiber 12 of such a configuration, the energy is not locally concentrated into the vicinity of the optical axis C. Even when components of vital hard tissues adhere to the emission end portion 22 of the optical fiber, i.e., the emission faces 23 and 24, the whole of the emission end portion 22 of the emission fiber 12 is heated and lost nearly uniformly. Therefore, in the case where vital hard tissues are to be evaporated by the laser treatment apparatus, even when components of vital hard tissues adhere to the emission end portion 22 of the optical fiber, the center portion of the emission end portion 22 of the emission fiber 12 can be prevented from being peeled off and damaged in a recessed shape. Also in a damaged emission end portion 22 of the emission fiber 12, the whole of the emission faces 23 and 24 of the emission fiber 12 is damaged in a nearly uniform manner. Therefore, the reduction of the evaporation ability due to a local heat generation in the emission faces 23 and 24 of the emission fiber 12 can be prevented from occurring.

Furthermore, the emission fiber 12 is configured as a three-layer structure in which the intermediate layer is formed between the core 30 and the clad 31. The refractive index of the clad 31 is lower than that of the center portion of the core 30, and the refractive index of the intermediate layer is lower than that of the clad 31. In the refractive index distribution of the whole of the emission fiber 12, the refractive index is sharply changed at the boundary between the core 30 and the intermediate layer and that between the intermediate layer and the clad 31. It is preferable that a laser beam which is used in a laser treatment apparatus for treating vital hard tissues has an energy density distribution which is uniform in a radial direction of a section of the core 30, in the emission end portion 22 of the emission fiber 12. When the intermediate layer is interposed between the core 30 and the clad 31, the energy density of the laser beam passed through the core 30 of the emission fiber 12 is sharply changed at positions corresponding to the boundaries between the core and the clad and the intermediate layer. Therefore, the energy is prevented from leaking into portions corresponding to the intermediate layer and the clad 31, with the result that the loss of the energy of the laser beam emitted from the emission end portion 22 of the emission fiber 12 is reduced. Consequently, the energy level of the laser beam entering the core 30 of the emission fiber 12 can be lowered by the level corresponding to the reduced loss.

In the above, though the embodiments in which the handpiece is used in the formation of a root canal have been described, the handpiece may be used in treatments such as the abscess treatment in the dental field, i.e., a treatment of removing away pus collecting in a periapex and the pulp amputation, irradiation on a wall in a narrow space for pollinosis in the field of otolaryngology, and the stone destruction in the field of an endoscopic treatment. Furthermore, the handpiece may be used in other treatments such as the evaporation of a bone or a cartilage, the removal of clots in a blood vessel, and the discission and evaporation of soft tissues in the digestive organs.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A medical laser handpiece comprising:
    a main body and a laser probe attached to the main body, the laser probe including an emission fiber including a core and a clad surrounding the core, a laser beam generated by a laser beam source being emitted from an emission end portion of the emission fiber, and wherein the emission end portion of the emission fiber is formed into a circular conical shape having a conical angle θ, and from the emission end portion are emitted a first laser beam in an axial direction of the emission fiber and a second laser beam in a ring-like shape in a radial direction of the emission fiber, and characterized in that:

a refractive index of an external space $n_0$, of the core $n_1$ and of the clad $n_2$ is each selected such that $\sin \phi_0 = n_0/n_1$ $\sin \phi_1 = n_2/n1$ $2(\phi_1 - \phi_0)$ is less than or equal to θ wherein $\phi_0$ is a critical angle of incidence of said laser beam with an inner surface of said circular conical shape and $\phi_1$ is a critical angle of incidence of said laser beam with an inner surface of said clad of the emission fiber;

whereby 1–20% of a laser beam entering the emission fiber is emitted as the first laser beam from the emission end portion, and 80–99% of the laser beam is emitted as the second laser beam from the emission end portion.

2. The medical laser handpiece of claim 1 characterized in that 5 to 15% of the laser beam entering the emission fiber is emitted as the first laser beam from the emission end portion, and 85 to 95% of the laser beam is emitted as the second laser beam from the emission end portion.

3. The medical laser handpiece according to claim 1, wherein a tip of said emission end portion is of a spherical shape and a radius of said spherical shape is proportional to a percentage of said laser beam entering said emission fiber which is emitted as said first laser bean.

4. A medical laser handpiece comprising:

a main body and a laser probe attached to the main body, the laser probe including an emission fiber including a core and a clad surrounding the core, a laser beam generated by a laser beam source being emitted from the core of an emission end portion of the emission fiber, and wherein the core of the emission end portion has a first emission face of a spherical shape forming a tip of the emission end portion, and from the first emission face are emitted a first laser beam in an axial direction of the emission fiber and a second emission face of a circular conical shape having a conical angle θ, from the second emission face are emitted a second laser beam in a ring-like shape in a radial direction of the emission fiber;

a refractive index of an external space $n_0$, of the core $n_1$ and of the clad $n_2$ is each selected such that $\sin \phi_0 = n_0/n_1$ $\sin \phi_1 = n_2/n_1$ $2(\phi_1 - \phi_0)$ is less than or equal to θ wherein $\phi_0$ is a critical angle of incidence of said laser beam with an inner surface of said circular conical shape and $\phi_1$ is a critical angle of incidence of said laser beam with an inner surface of said clad of the emission fiber;

the first and the second emission faces are formed so as to be tangential to each other over the whole periphery with respect to the optical axis, and a sectional area ratio of a first area of a section including the boundary line of the first and the second emission faces to a second area of the whole of the core is chosen to be 1–20%.

5. The medical laser handpiece of claim 1 or 4 wherein an apex angle of the circular conical shape of the emission fiber is in a range of 60 to 93 degrees.

6. The medical laser handpiece of claim 1 or 4 wherein an apex angle of the circular conical shape of the emission fiber is in a range of 60 to 90 degrees.

7. The medical laser handpiece of claim 1 or 4 wherein an apex angle of the circular conical shape of the emission fiber is in a range of 70 to 80 degrees.

8. The medical laser handpiece of claim 1 or 4, characterized in that the second laser beam emitted from the emission end portion of the emission fiber is emitted in a radial direction nearly perpendicular to the axis of the emission fiber.

9. The medical laser handpiece of claim 1 or 4, characterized in that the first laser beam emitted from the emission end portion of the emission fiber is emitted in a ring-like shape in the axial direction of the emission fiber.

10. The medical laser handpiece of claim 1 or 4, characterized in that an electrode made of an electrically conductive material is disposed on an outer periphery of the emission fiber.

11. The medical laser handpiece of claim 1 or 4, characterized in that the emission fiber has an outer diameter of 100 to 2,000 μm and the laser probe is a probe for a dental treatment.

* * * * *